(12) United States Patent
Fehling

(10) Patent No.: US 10,441,424 B2
(45) Date of Patent: Oct. 15, 2019

(54) GAUGE FOR THE RECONSTRUCTION OF A CUSP OF AN AORTIC VALVE

(71) Applicant: FEHLING INSTRUMENTS GMBH & CO. KG, Karlstein (DE)

(72) Inventor: Gerald Fehling, Alzenau (DE)

(73) Assignee: VEGA GRIESHABER KG, Wolfach (DE)

( * ) Notice: Subject to any disclaimer, the term of this patent is extended or adjusted under 35 U.S.C. 154(b) by 148 days.

(21) Appl. No.: 15/678,189

(22) Filed: Aug. 16, 2017

(65) Prior Publication Data

US 2018/0125660 A1    May 10, 2018

(30) Foreign Application Priority Data

Oct. 14, 2016 (DE) .................. 10 2016 119 620

(51) Int. Cl.
| | | |
|---|---|---|
| *A61B 5/107* | (2006.01) | |
| *A61F 2/24* | (2006.01) | |
| *A61B 90/00* | (2016.01) | |

(52) U.S. Cl.
CPC .......... *A61F 2/2496* (2013.01); *A61B 5/1076* (2013.01); *A61B 90/06* (2016.02); *A61F 2/2412* (2013.01); *A61F 2/2448* (2013.01); *A61F 2240/002* (2013.01)

(58) Field of Classification Search
CPC .................................................. A61F 2/2496

USPC ..................................................... 33/512, 563
See application file for complete search history.

(56) References Cited

U.S. PATENT DOCUMENTS

| | | | |
|---|---|---|---|
| 6,378,221 B1 * | 4/2002 | Ekholm, Jr. ........... | G01B 5/207 33/121 |
| 2002/0020074 A1 | 2/2002 | Love | |
| 2005/0085904 A1 * | 4/2005 | Lemmon ............... | A61F 2/2427 623/2.11 |
| 2005/0283232 A1 * | 12/2005 | Gabbay ................ | A61B 5/1076 623/2.11 |
| 2006/0229716 A1 * | 10/2006 | Mitrev ................. | A61B 5/1072 623/2.11 |
| 2009/0192600 A1 | 7/2009 | Ryan | |
| 2009/0192602 A1 | 7/2009 | Kuehn | |
| 2012/0179247 A1 * | 7/2012 | Navia ................... | A61F 2/2445 623/2.37 |
| 2016/0206428 A1 * | 7/2016 | Ryan ..................... | A61F 2/2496 |
| 2017/0084029 A1 * | 3/2017 | Piazza .................. | A61B 5/1075 |
| 2019/0053906 A1 * | 2/2019 | Liljegren .............. | A61F 2/2496 |

OTHER PUBLICATIONS

GPTO Office Action for related German application 10 2016 119 620.7, dated Jul. 19, 2017.

\* cited by examiner

*Primary Examiner* — George B Bennett
(74) *Attorney, Agent, or Firm* — William Gray Mitchell

(57) ABSTRACT

The invention is a gauge for the reconstruction of a cusp of an aortic valve, with the gauge (10) being made from a material that can be deformed in a plastic fashion using manual force.

14 Claims, 1 Drawing Sheet

GAUGE FOR THE RECONSTRUCTION OF A CUSP OF AN AORTIC VALVE

CROSS REFERENCE TO RELATED APPLICATIONS

This patent application claims priority to German Patent Application 10 2016 119 620.7, filed on Oct. 14, 2016.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The invention is a gauge for the reconstruction of a cusp of an aortic valve.

Background of the Invention

The aortic valve (valva aortae) is arranged as a valve system in the aortic opening of the left ventricle, which opens with the systole under the ventricular pressure of the blood and closes with the diastole under the arterial pressure. The aortic valve usually comprises three valvular cusps, which are connected separately via commissures at the annulus fibrosus. The valvular cusps tightly abut each other with their free edges in the closed position in order to prevent any blood reflux out of the aorta into the left ventricle. In the open position the free edges of the elastic flexible cusp are moved away from each other.

Defects of the aortic valve can be treated with different surgical procedures. The defective aortic valve can be replaced completely or partially by a mechanical or biological prosthetic valve. Here, it is known in particular to replace individual cusps of an aortic valve.

In order to allow determining the size of the implant for the cusp of the aortic valve, standardized gauges are known in prior art as means to define the size required to support the surgeon in the reconstruction and to shorten the length of the operation.

Known gauges are made from a stiff synthetic, which show for example the shape of a flat, outstretched cusp of an aortic valve and which are made available in different sizes in order to provide the surgeon during the operation with an indication of which size and shape must be selected for the implant material in order to reconstruct the cusp of the aortic valve. A set of several such gauges with different sizes is known from prior art, with here the diameter of the annulus, for which the respective size of the gauge would be suitable, being marked on the gauges. During the operation, the diameter of the annulus of the patient is determined and then the appropriate gauge is selected. The gauge can be used like a template in order to then transfer the size and shape to the implant material and to allow a foundation for the reconstruction. However, usually the gauge fails to provide the exact shape and size of the cusp of the valve, because the actually required shape and size is determined by the surgeon during the operation based on the actual anatomic conditions.

The objective of the invention is to provide a gauge for the reconstruction of a cusp of an aortic valve, which allows a better estimate of the size and shape of the aortic valve cusp implant. In particular, a faster assessment will be possible to shorten the duration of the operation.

The objective is attained according to the invention in a gauge for the reconstruction of a cusp of an aortic valve with the features as described herein.

BRIEF SUMMARY OF THE INVENTION

In a preferred embodiment, a gauge (10) for the reconstruction of a cusp of an aortic valve, characterized in that the gauge (10) is made from a material that can be deformed in a plastic fashion upon manual force being applied.

In another preferred embodiment, the gauge (10) as described herein, characterized in that the gauge is made from a bio-compatible material.

In another preferred embodiment, the gauge (10) as described herein, characterized in that the gauge (10) is made from a material that can be sterilized.

In another preferred embodiment, the gauge (10) as described herein, characterized in that the gauge (10) is made from a material with bending characteristics exceeding 10 degrees.

In another preferred embodiment, the gauge (10) as described herein, characterized in that the gauge (10) is made from a flexible steel, flexible aluminum, or flexible synthetic material.

In another preferred embodiment, the gauge (10) as described herein, characterized in that the gauge (10) is made from a nickel-titanium alloy.

In another preferred embodiment, the gauge (10) as described herein, characterized in that the gauge (10) is made of a memory alloy.

In another preferred embodiment, the gauge (10) as described herein, characterized that the gauge (10) has a thickness (d) ranging from 0.05 mm to 2 mm, advantageously a thickness (d) ranging from 0.25 mm to 0.45 mm, preferably a thickness (d) ranging from 0.30 mm to 0.36 mm, for example a thickness (d) of 0.33 mm.

In another preferred embodiment, the gauge (10) as described herein, characterized in that the gauge (10) shows a width (b) ranging from 15 mm to 40 mm.

In another preferred embodiment, the gauge (10) as described herein, characterized in that the gauge (10) comprises at its exterior perimeter at least one, preferably several, particularly three recesses (15).

In another preferred embodiment, the gauge (10) as described herein, characterized in that the gauge (10) has rounded edges to prevent trauma.

In an alternate preferred embodiment, a set comprising several gauges (10) as described herein, in various sizes.

DETAILED DESCRIPTION OF THE INVENTION

Figure 1:
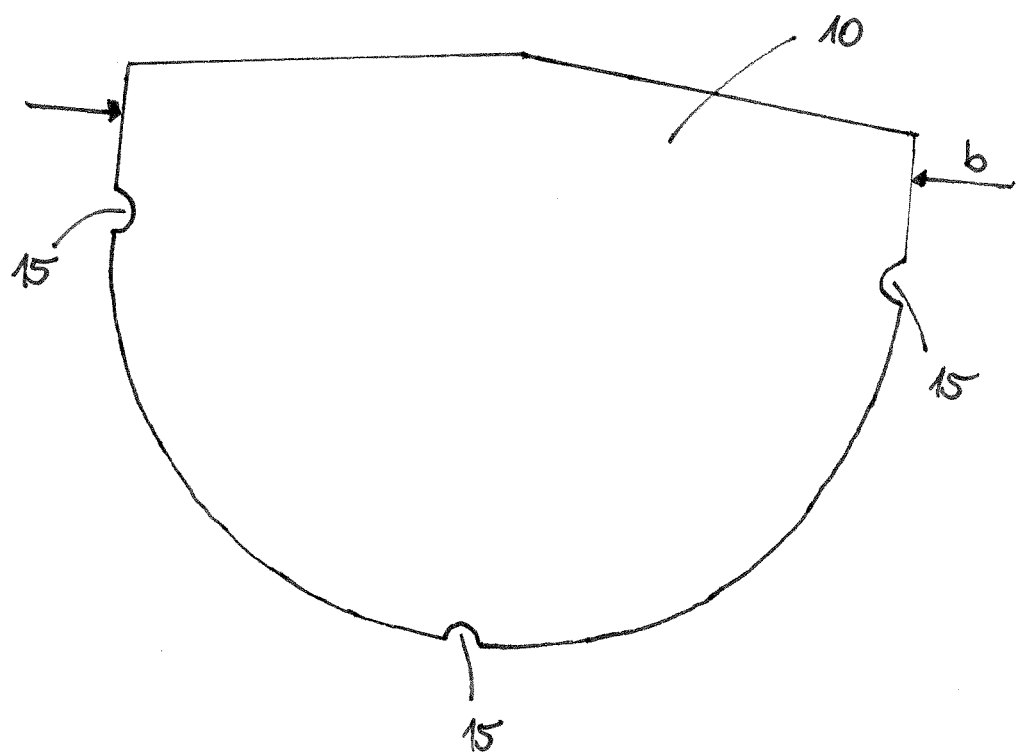
FIG. 1 is a line drawing evidencing a top view of an exemplary embodiment of a gauge according to the invention for the reconstruction of a cusp of an aortic valve.

The gauge according to the invention for the reconstruction of a cusp of an aortic valve is made from a material that can be deformed in a plastic fashion upon manual force being applied. This offers the opportunity for the surgeon, during the operation, to deform the gauge manually with little force in order to reconstruct the spacial shape of the cusp to be replaced and to get a better model thereof. Although the stiff gauges of prior art show the shape of the cusp to be replaced, they are, however, provided in the form of a cusp spread in a level, while the cusp in the state sutured to the aortic valve shows a curved shape. Due to the fact that the gauge is made from a material that can be deformed in a plastic fashion, the surgeon can also reconstruct the spatial shape of the cusp to be replaced so that the required size can generally be determined faster and more precisely. Furthermore, the plastic deformation of the gauge allows that after the determination of the optimal size of the gauge, here the gauge can be bent back flat and thus can be placed flat onto the implant material in order to mark the size of the desired implant with the help of the gauge on said implant material and cut the implant material to the desired size.

The gauge is preferably made from a bio-compatible material for safety reasons and to protect the patient.

Preferably the gauge is made from a material that can be sterilized in order to allow cleaning the gauge after the operation and allow reuse thereof.

Advantageously the gauge is made from a material showing bending features of more than 10 degrees. That means particularly that the material can be bent by an angle of 10 degrees or more without flaking or breaking. For example, the gauge can be made from a flexible steel, flexible aluminum, or flexible synthetic material, with a manual deformation of the material being possible without the use of a machine.

It is particularly preferred that the gauge is made from a nickel-titanium alloy, which represents an example of a material that is both deformable in a plastic fashion as well as bio-compatible and which allows sterilization.

According to a particularly preferred further development of the invention, the gauge is made from a memory alloy. A memory alloy has the advantage that it is deformable in a plastic fashion at a temperature, for example room temperature, and upon exceeding a higher upper transition temperature it returns back to its original shape. If the gauge is made from such a material, it can be deformed during the operation into the desired shape, and during a subsequent cleaning and sterilizing process, which generally occurs at a temperature exceeding the higher upper transition temperature, it returns to its original shape.

The gauge advantageously has a thickness ranging from 0.05 mm to 2 mm, advantageously a thickness ranging from 0.25 mm to 0.45 mm, preferably a thickness ranging from 0.3 mm to 0.36 mm, for example a thickness amounting to 0.33 mm, in order to allow reconstructing the thickness of the cusp of the aortic valve as accurately as possible.

Advantageously the gauge has a width ranging from 15 mm to 40 mm in order to allow reconstruction of the common width of cusps of aortic valves.

A particularly preferred further development of the invention provides that the gauge shows at its exterior perimeter at least one, preferably several, particularly three recesses. The recesses may represent markers, for example to determine the commissure and the center of the implant. With such markers it is easier for the surgeon to correctly align the implant to be inserted to the commissure.

Preferably the gauge shows traumatically rounded edges in order to prevent any damages of the implant material or the patient.

According to the invention, a set comprising several gauges according to the invention in different sizes is provided in order to render several gauges of different sizes available to the surgeon during the operation, based on which he/she can optimally determine the matching size of the aortic valve cusp implant to be inserted.

DETAILED DESCRIPTION OF THE FIGURES

Figure 2:
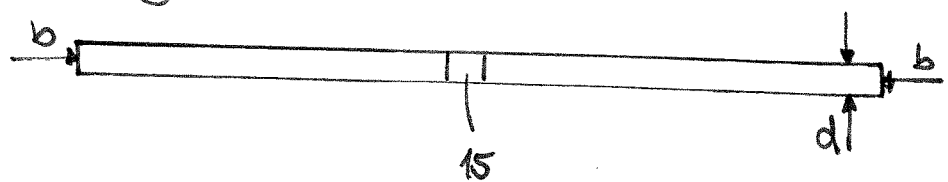
FIG. 2 is a line drawing evidencing a side view of the gauge according to FIG. 1.

An exemplary embodiment of a gauge 10 according to the invention for the reconstruction of a cusp of an aortic valve is shown in FIGS. 1 and 2. The gauge 10 shows approximately the exterior contour of a cusp of an aortic valve in a state stretched out in a planar fashion. The contour of the cusp 10 may show two straight lines arranged at an obtuse angle, with their free ends being connected to each other by a curved line, for example at least sectionally a circular line.

The gauge 10 according to the invention is made from a material that can be deformed in a plastic fashion. This shall be understood as a material that can be deformed in a plastic fashion, which irreversibly deforms under the influence of force and maintains this shape even after this force has subsided. By a renewed application of force the material can be further deformed and can also be returned into the original condition. Here, the application of manual force shall be sufficient for the deformation so that plastic deformation can occur without the help of a machine.

The gauge 10 may be made from a bio-compatible material. Further, the gauge 10 may be made from a material that can be sterilized. The gauge is, for example, made from a material with bending characteristics of more than 10 degrees. This means particularly that the material can be bent by an angle of 10 degrees or more without flaking or breaking. For example, the gauge may be made from a flexible steel, flexible aluminum, or flexible synthetic, with the material selected respectively allowing manual plastic deformation.

According to one embodiment, the gauge 10 may be made from a memory alloy such that the gauge 10 can be deformed in a plastic fashion at room temperature and upon an upper transition temperature being exceeded, which is above room temperature, returns to its original shape. During the operation, the surgeon can therefore bend the gauge 10 into the desired shape. The gauge 10 maintains this shape until it is either deformed further or also deformed flat by the surgeon, the latter for example in order to allow transferring the shape of the gauge 10 to the implant material by tracing it. If the gauge 10 is cleaned during the preparation of the instruments in a washing machine or an autoclave and here the upper transition temperature is exceeded, the gauge 10 returns to its original shape.

For example, the gauge may be made from a nickel-titanium alloy.

The gauge 10 may show a thickness d from 0.05 mm to 2 mm, advantageously a thickness from 0.25 mm to 0.45 mm, preferably a thickness d at a range from 0.3 mm to 0.36 mm, for example having a thickness d of 0.33 mm. The gauge 10 may show a width b ranging from 15 mm to 40 mm.

One embodiment of the gauge 10 comprises at its exterior perimeter, particularly in the curved part of the exterior perimeter, at least one, preferably several, in the present exemplary embodiment three recesses 15. The recesses 15 form markers. In particular, the three markers 15 can be arranged according to the exemplary embodiment of the gauge 10 illustrated in FIG. 1 such that one of the markers identifies the axis of symmetry of the implant 10 and thus the center of the implant, while the two other markers 15, arranged symmetrically at the lateral areas of the gauge 10, identify the commissure. Such markers 15 make it easier for the surgeon to align the implant, cut with the help of the gauge 10, correctly at the commissure. In particular, the three markers 15 can identify the two highest and the lowest point of the commissure.

To avoid trauma, the edges of the gauge 10 can be embodied in a rounded form in order to prevent any damages of the implant material and injuries of the patient.

According to the invention, a set of several gauges having different sizes is made available.

The gauge 10 according to the invention can be used as follows.

If a defective aortic valve cusp is to be replaced in a surgical procedure, the implant material, for example autologous pericardium, shall be cut to the desired shape and size and then inserted in the place of the removed defective aortic valve cusp and fastened there by sutures. In order to provide the surgeon with means for determining the correct size and shape of the aortic valve cusp implant to be inserted, gauges have been developed for the reconstruction of a cusp of an aortic valve. The use of such gauges accelerates particularly the process of adjustment and avoids long adaptation periods.

Once the defective aortic valve cusp has been removed during the operation, the surgeon can initially select from a set of gauges 10 according to the invention, using visual judgment, a gauge 10 matching as closely as possible, adjust it by appropriate manual deformation to the anatomic conditions, and hold it to the annulus of the aortic valve in order to determine if the size of the selected gauge 10 matches optimally. If necessary, the process can be repeated with a larger or smaller gauge 10.

Once the optimally matching size of the gauge 10 has been determined, the gauge 10 selected in this fashion can be returned into a flat state and the shape of the gauge 10 can be transferred to the implant material, e. g. autologous pericardium, by tracing the gauge 10 with a pen. The recesses 15 included in the gauge 10 can here indicate the commissure and the center of the implant on the implant tissue such that the orientation of the surgeon is supported when inserting the aortic valve cusp implant cut from the implant tissue.

Due to the fact that the gauge is made from a material that can be deformed in a plastic fashion, the surgeon can better reconstruct during the operation the actual anatomic shape of the aortic valve cusp and adjust the desired size more easily to the anatomic conditions. The optimal size of the gauge 10 can be selected more quickly and easily, thus the duration of the operation is shortened so that the invasive surgery of the patient can be reduced and the recovery of the patient is therefore improved. Additionally, the plastic deformation of the material facilitates the subsequent transfer of the shape and size of the gauge 10 selected to the implant material. Simple handling is the result here particularly when the material that can be deformed in a plastic fashion can be deformed at room temperature using manual force.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

I claim:

1. A gauge for the reconstruction of a cusp of an aortic valve, characterized in that the gauge is made from a material that can be deformed in a plastic fashion upon manual force being applied.

2. The gauge according to claim 1, wherein the gauge is made from a bio-compatible material.

3. The gauge according to claim 1, wherein the gauge is made from a material that can be sterilized.

4. The gauge according to claim 1, wherein the gauge is made from a material with bending characteristics exceeding 10 degrees.

5. The gauge according to claim 1, wherein the gauge is made from a flexible steel, flexible aluminum, or flexible synthetic material.

6. The gauge according to claim 1, wherein the gauge is made from a nickel-titanium alloy.

7. The gauge according to claim 1, wherein the gauge is made of a memory alloy.

8. The gauge according to claim 1, wherein the gauge has a thickness ranging from 0.05 mm to 2 mm.

9. The gauge according to claim 1, wherein the gauge shows a width ranging from 15 mm to 40 mm.

10. The gauge according to claim 1, wherein the gauge comprises at its exterior perimeter between one and three recesses.

11. The gauge according to claim 1, wherein the gauge has rounded edges to prevent trauma.

12. A set comprising several gauges according to claim 1, in various sizes.

13. The gauge according to claim 1, wherein the gauge shows a thickness from 0.25 mm to 0.45 mm.

14. The gauge according to claim 1, wherein the gauge shows a thickness from 0.30 mm to 0.36 mm.

* * * * *

UNITED STATES PATENT AND TRADEMARK OFFICE
CERTIFICATE OF CORRECTION

PATENT NO. : 10,441,424 B2  
APPLICATION NO. : 15/678189  
DATED : October 15, 2019  
INVENTOR(S) : Gerald Fehling It is certified that error appears in the above-identified patent and that said Letters Patent is hereby corrected as shown below:

On the Title Page

Item (73), Please change the current named assignee to the following:  
Assignee: FEHLING INSTRUMENTS GMBH & CO. KG, Karlstein (DE)

Signed and Sealed this
Twenty-fourth Day of December, 2019

Andrei Iancu
*Director of the United States Patent and Trademark Office*